United States Patent
Venkata Chilukuri et al.

(10) Patent No.: US 9,944,617 B2
(45) Date of Patent: Apr. 17, 2018

(54) SELECTIVE AEROBIC OXIDATIONS USING CARBON NITRIDE NANOTUBES

(71) Applicant: Council of Scientific and Industrial Research, New Delhi (IN)

(72) Inventors: Satyanarayana Vera Venkata Chilukuri, Pune (IN); Narasimharao Kanna, Pune (IN); Lakshmiprasad Gurrala, Pune (IN)

(73) Assignee: COUNCIL OF SCIENTIFIC AND INDUSTIAL RESEARCH, New Delhi (IN)

( * ) Notice: Subject to any disclaimer, the term of this patent is extended or adjusted under 35 U.S.C. 154(b) by 0 days.

(21) Appl. No.: 15/101,277

(22) PCT Filed: Dec. 2, 2014

(86) PCT No.: PCT/IN2014/000747
§ 371 (c)(1),
(2) Date: Jun. 2, 2016

(87) PCT Pub. No.: WO2015/083185
PCT Pub. Date: Jun. 11, 2015

(65) Prior Publication Data
US 2016/0304484 A1    Oct. 20, 2016

(30) Foreign Application Priority Data
Dec. 2, 2013   (IN) .......................... 3490/DEL/2013

(51) Int. Cl.
C07C 45/33    (2006.01)
C07C 51/31    (2006.01)
C07D 313/04   (2006.01)
B01J 27/24    (2006.01)

(52) U.S. Cl.
CPC ............ *C07D 313/04* (2013.01); *B01J 27/24* (2013.01); *C07C 45/33* (2013.01); *C07C 51/313* (2013.01)

(58) Field of Classification Search
CPC ....... C07C 51/313; C07C 55/14; C07C 45/33; B01J 27/24; C07D 313/04
See application file for complete search history.

(56) References Cited

FOREIGN PATENT DOCUMENTS

WO    WO-2015/083185    6/2015

OTHER PUBLICATIONS

Yu et al., "Selective Catalysis of the Aerobic Oxidation of Cyclohexane in the Liquid Phase by Carbon Nanotubes," Angew. Chem. Int. Ed. 2011, 50, 3978-3982.*

Cao, Yonghai, et al., "Nitrogen-, phosphorous- arid boron-doped carbon nanotubes as catalysts for the aerobic oxidation of cyclohexane", "Carbon", 57, (Jun. 2013), 433-442.

Li, Xin-Hao, et al., "Metal-Free Activation of Dioxygen by Graphene/g-$C_3N_4$ Nanocomposites: Functional Dyads for Selective Oxidation of Saturated Hydrocarbons", *J. Am. Chem. Soc.*, 133(21), (2011), 8074-8077.

Li, Xin-Hao, et al., "Solvent-Free and Metal-Free Oxidation of Toluene Using $O_2$ and g-$C_3N_4$ with Nanopores: Nanostructure Boosts the Catalytic Selectivity", *ACS Catalysis*, 2(10), (2012), 20825-2086.

Li, Yue-Fang, et al., "Graphite as a highly efficient and stable catalyst for the production of lactones", *Carbon*, 55, (Apr. 2013), 269-275.

Wang, Yong, et al., "Boron- and Fluorine-Containing Mesoporous Carbon Nitride Polymers: Metal-Free Catalysts for Cyclohexane Oxidation", *Angew. Chem. Int. Ed.*, 49(19), (2010), 3356-3359.

Yu, Hao, et al., "Selective Catalysis of the Aerobic Oxidation of Cyclohexane in the Liquid Phase by Carbon Nanotubes", *Angew. Chem. Int. Ed.*, 50(17), (2011), 3978-3982.

"International Application No. PCT/IN2014/000747, International Search Report and Written Opinion dated Mar. 25, 2015", (Mar. 25, 2015), 8 pgs.

* cited by examiner

*Primary Examiner* — Pancham Bakshi
*Assistant Examiner* — Mark R Luderer
(74) *Attorney, Agent, or Firm* — Schwegman Lundberg & Woessner, P.A.

(57) ABSTRACT

The present invention discloses an improved oxidation process using carbon nitride nanotubes as metal free catalyst and molecular O2 as the oxidant to obtain desired adipic acid and other oxygenated hydrocarbons with improved conversion and selectivity.

10 Claims, 13 Drawing Sheets

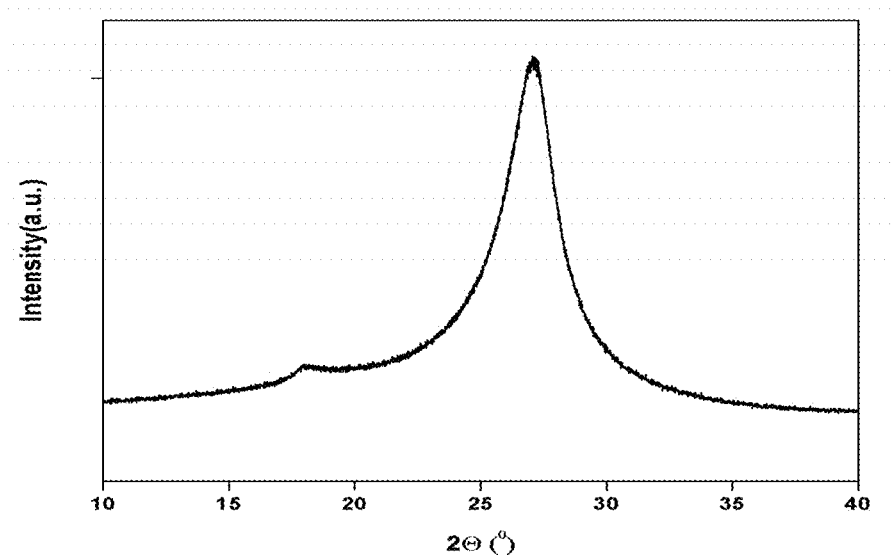
Fig: 1
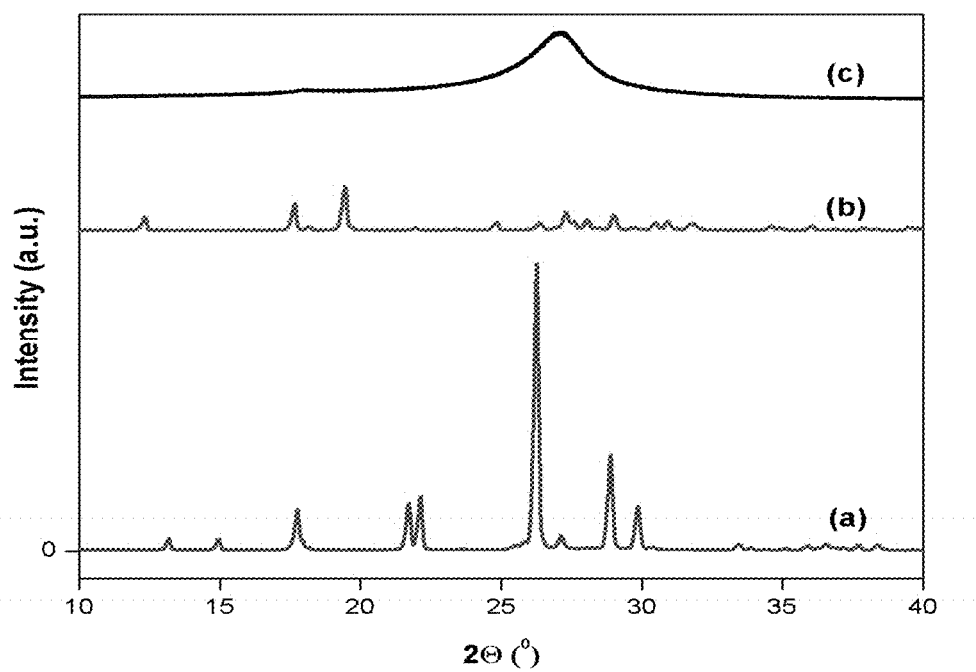
Fig: 2

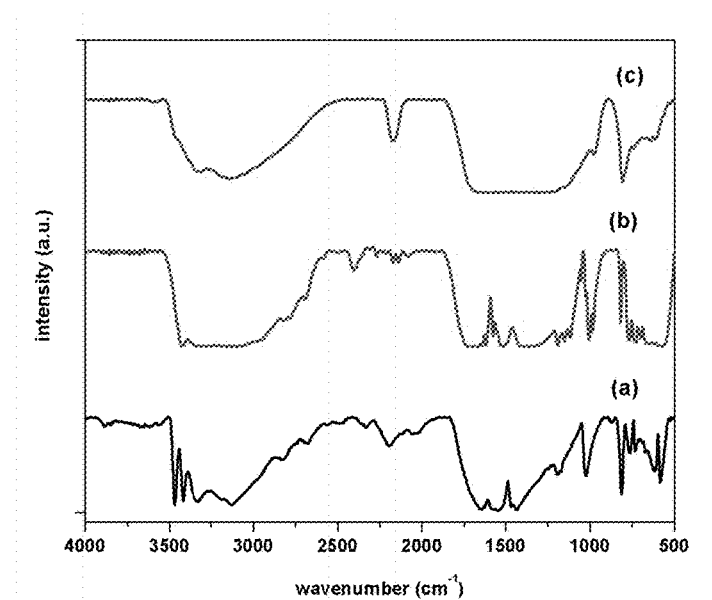
Fig: 3
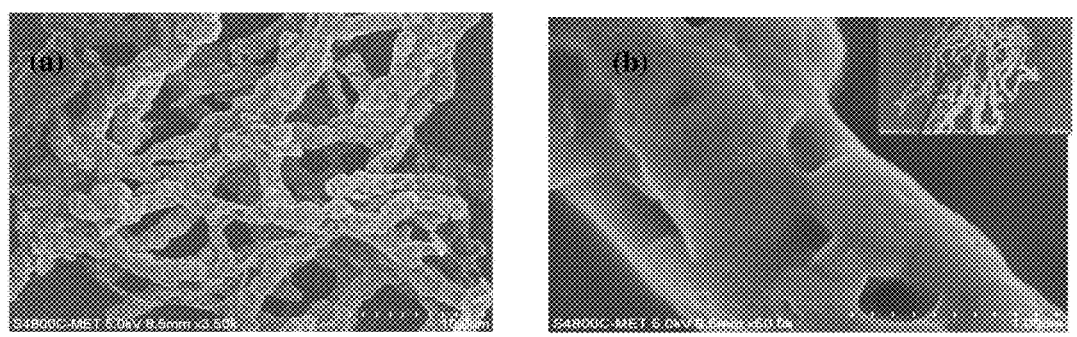
Fig: 4

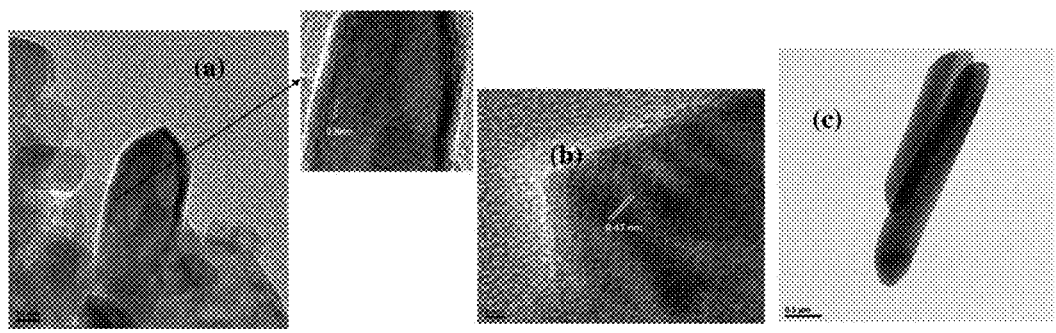
Fig: 5
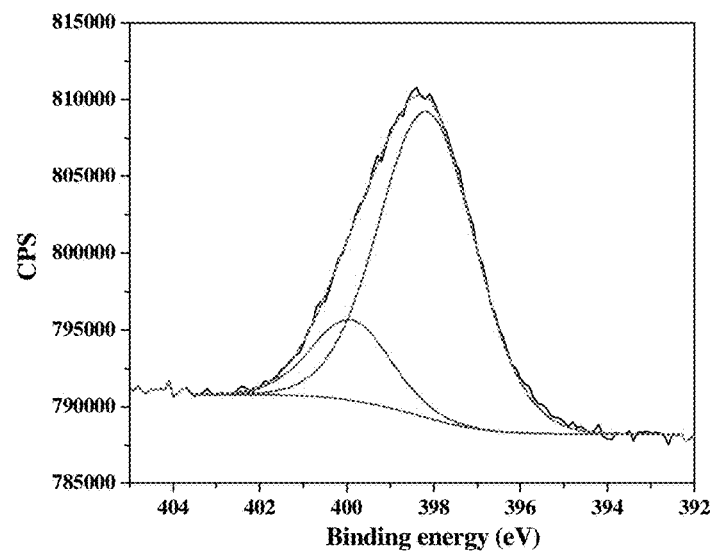
Fig: 6

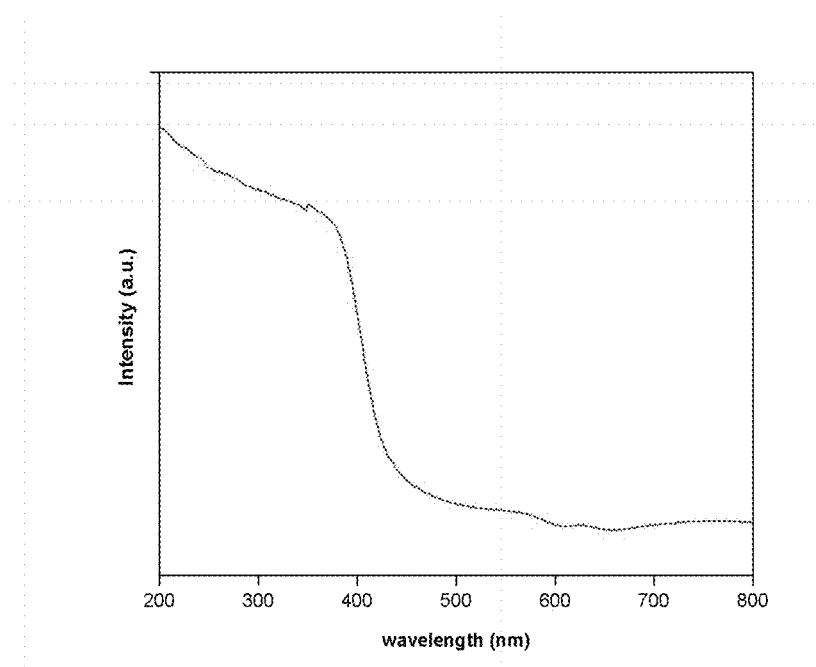
Fig: 7
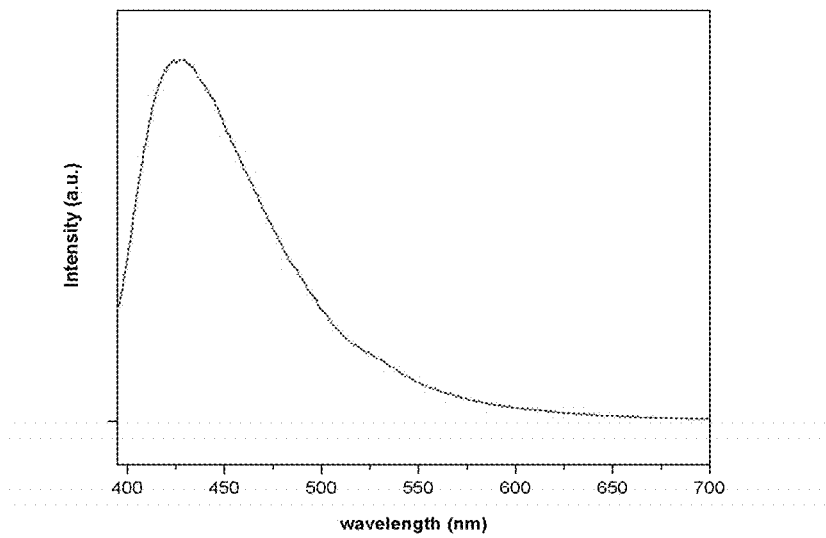
Fig: 8

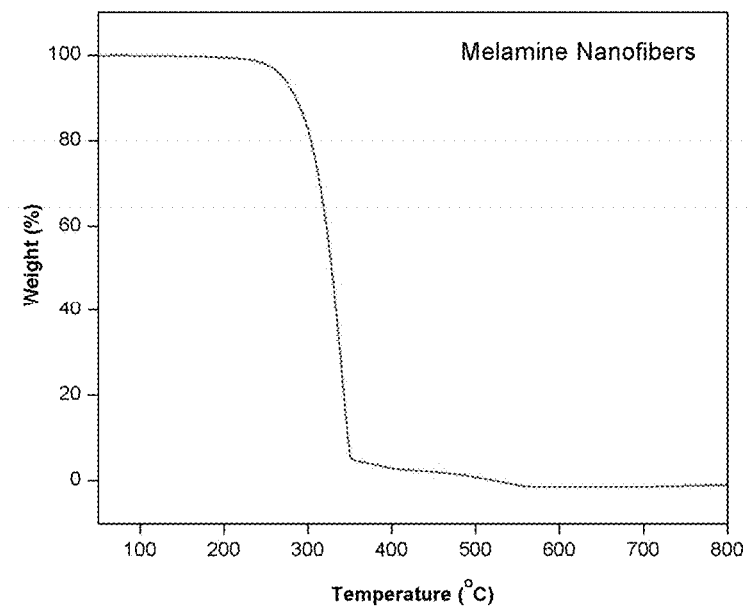
Fig: 9
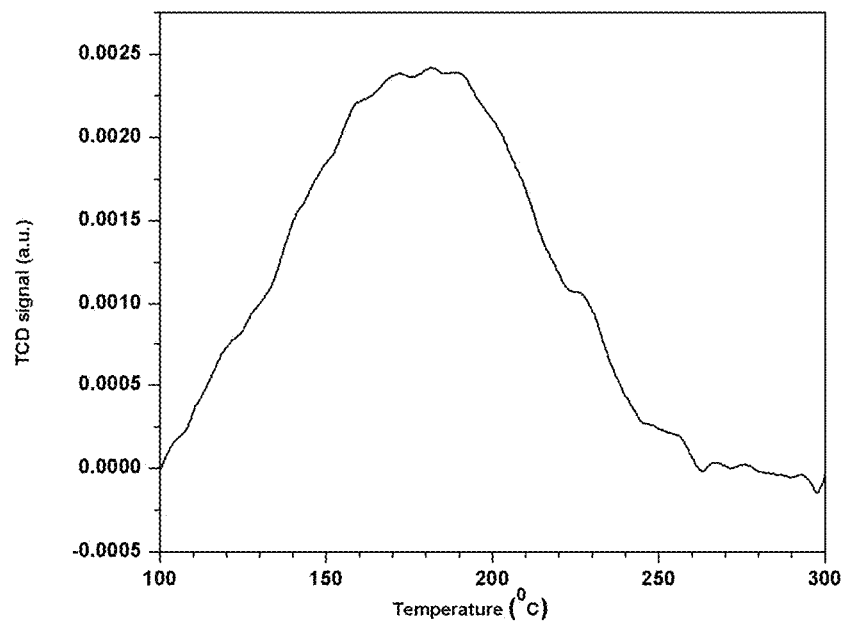
Fig: 10

(a)
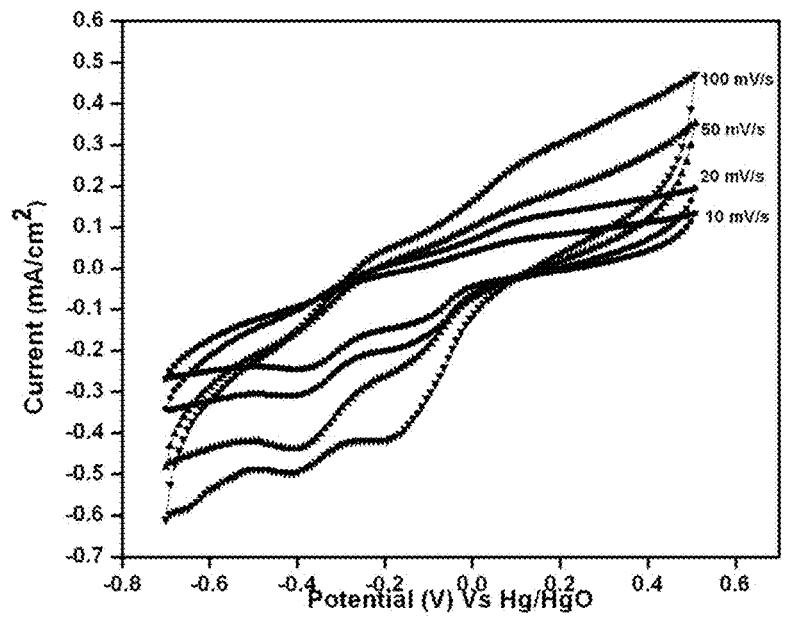
(b)
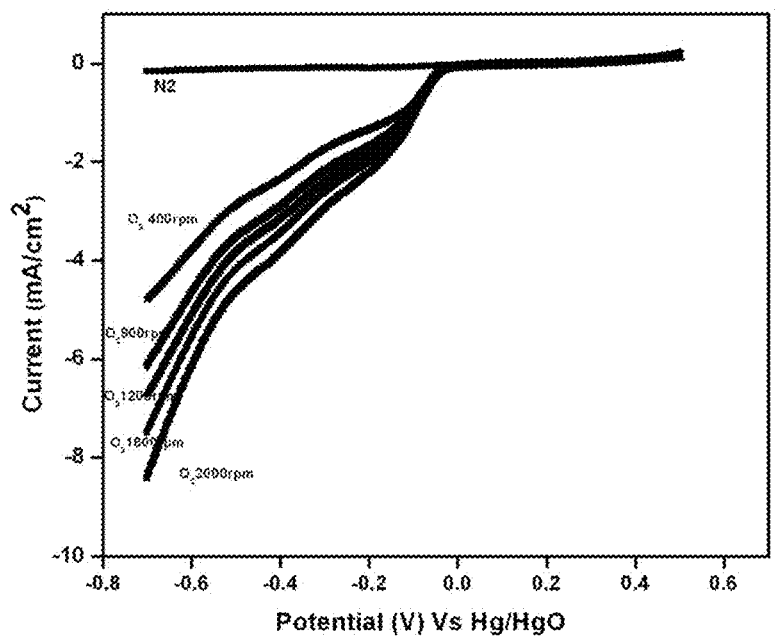
Fig: 11

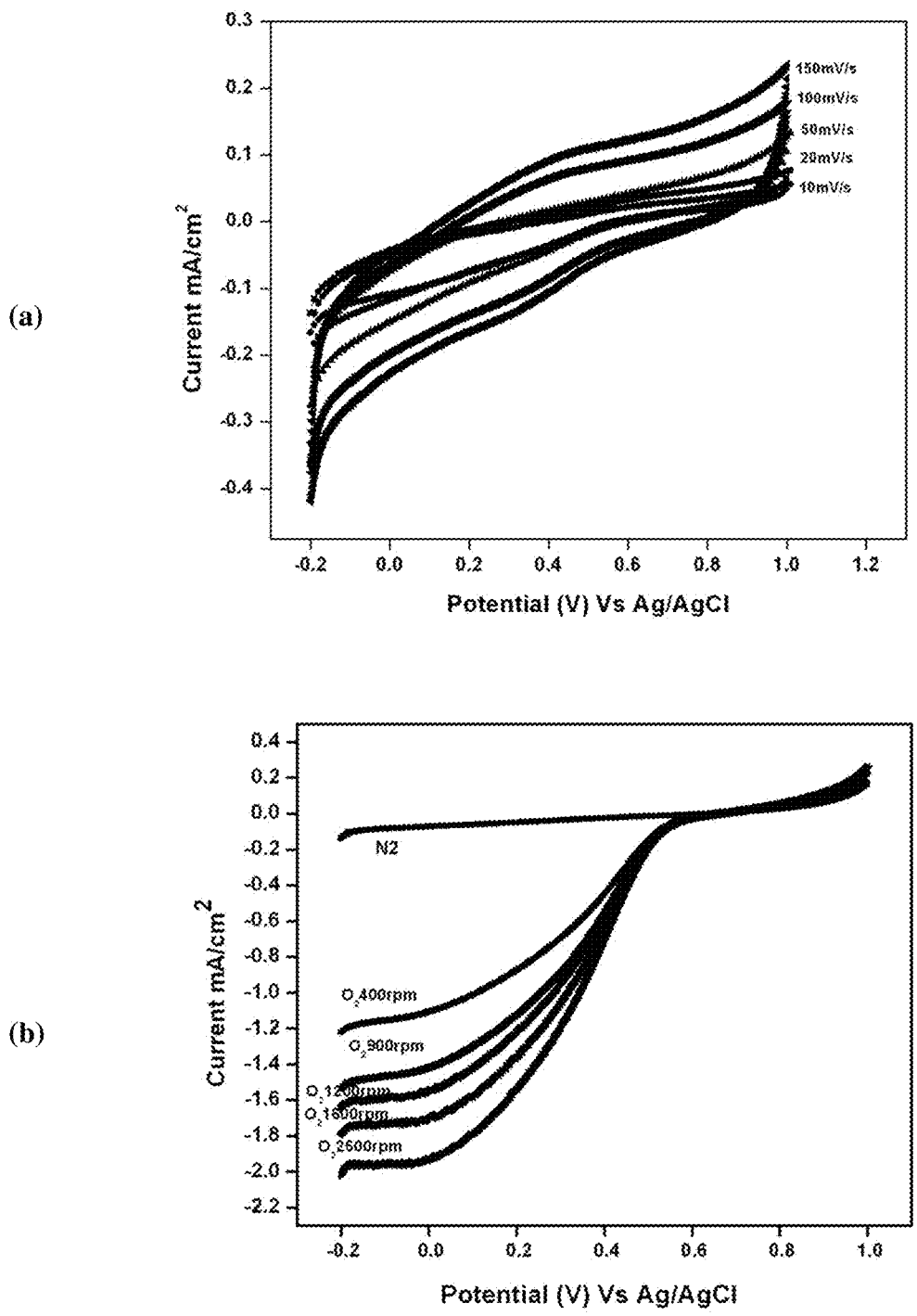
Fig: 12

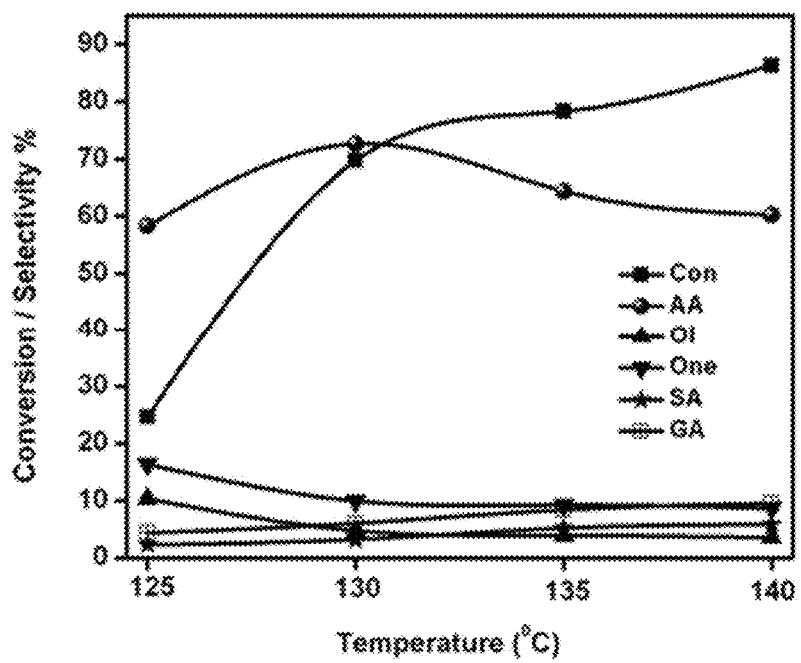
Fig: 13
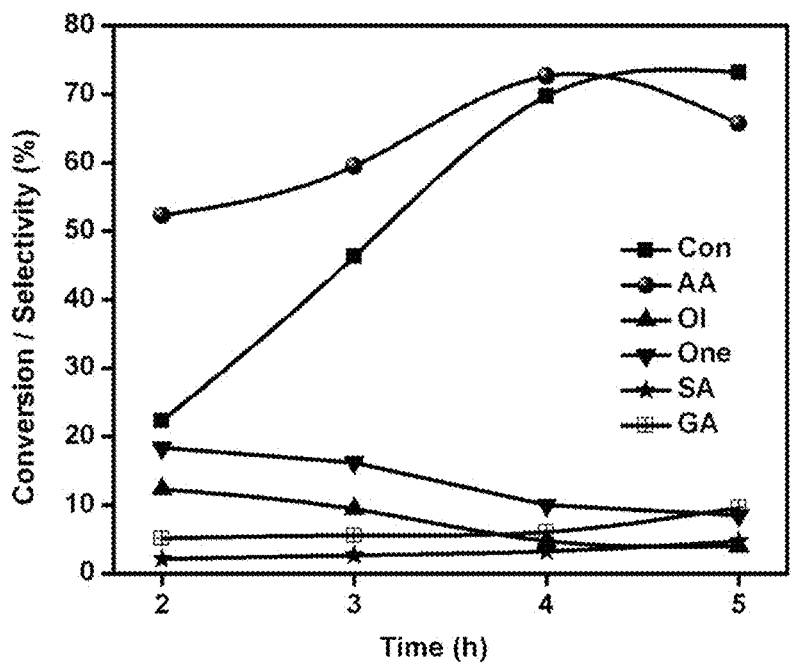
Fig: 14

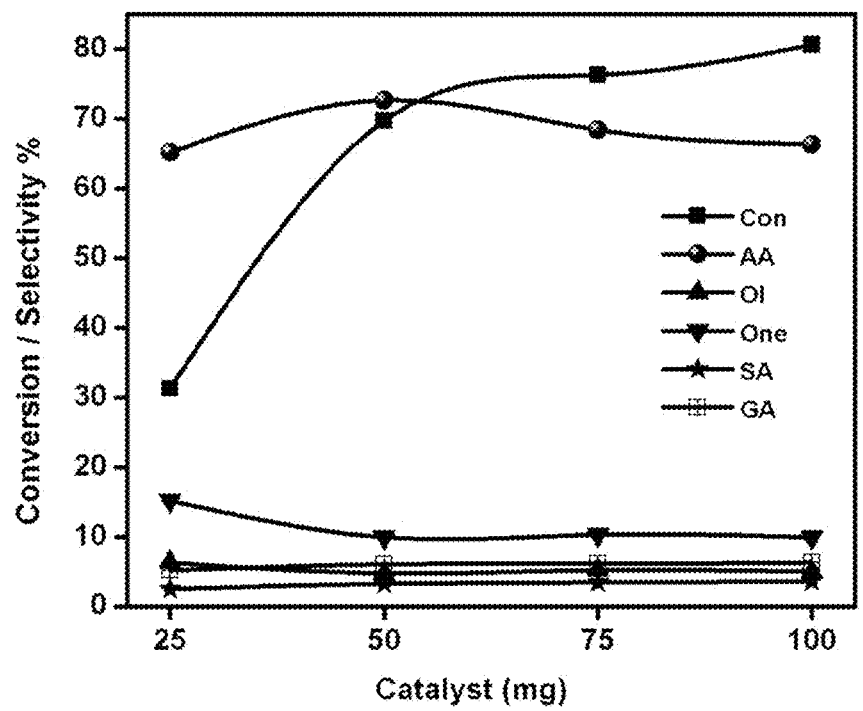
Fig: 15
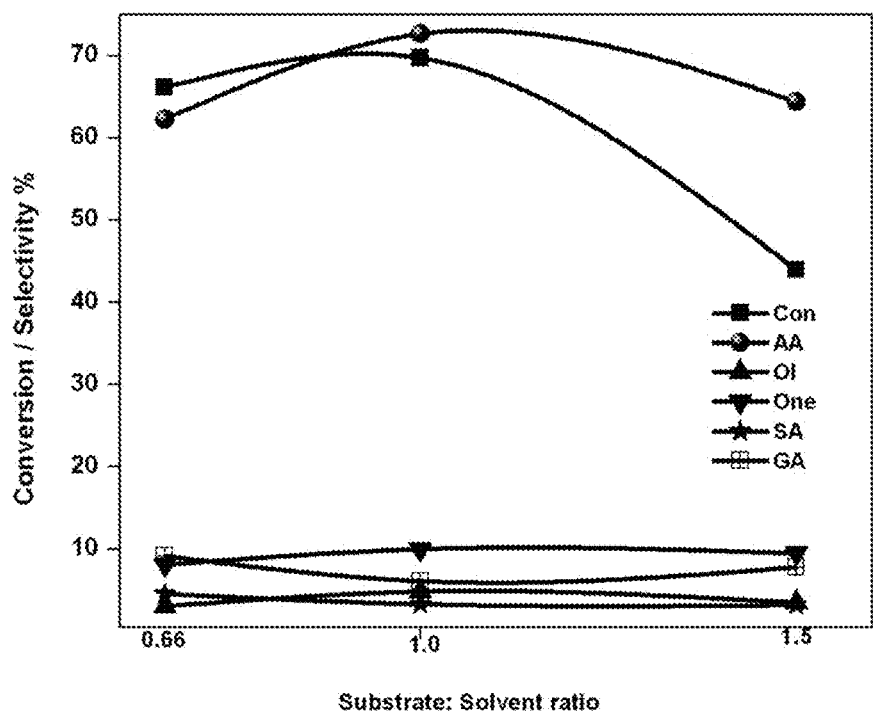
Fig: 16

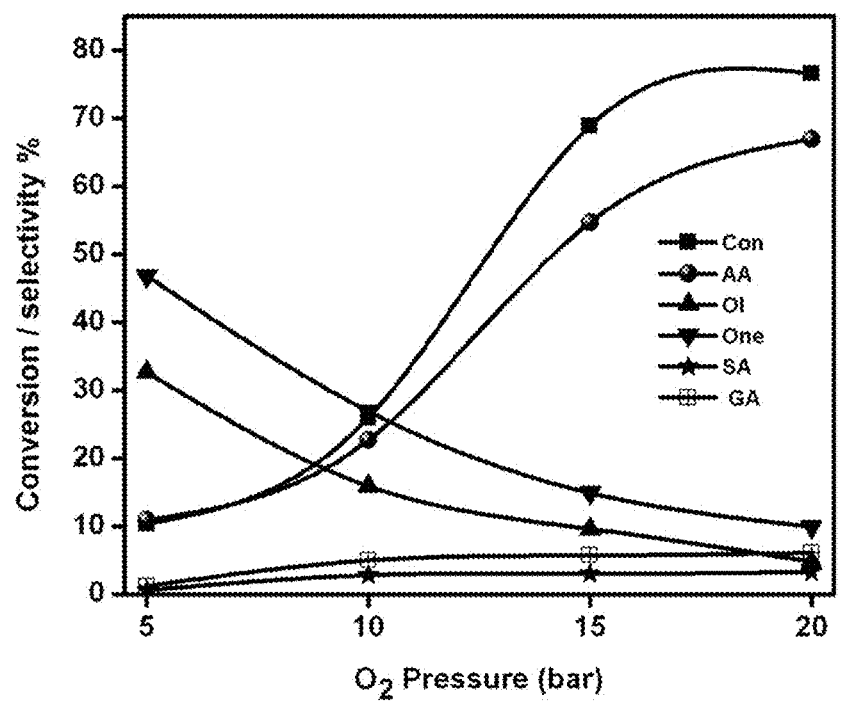
Fig: 17
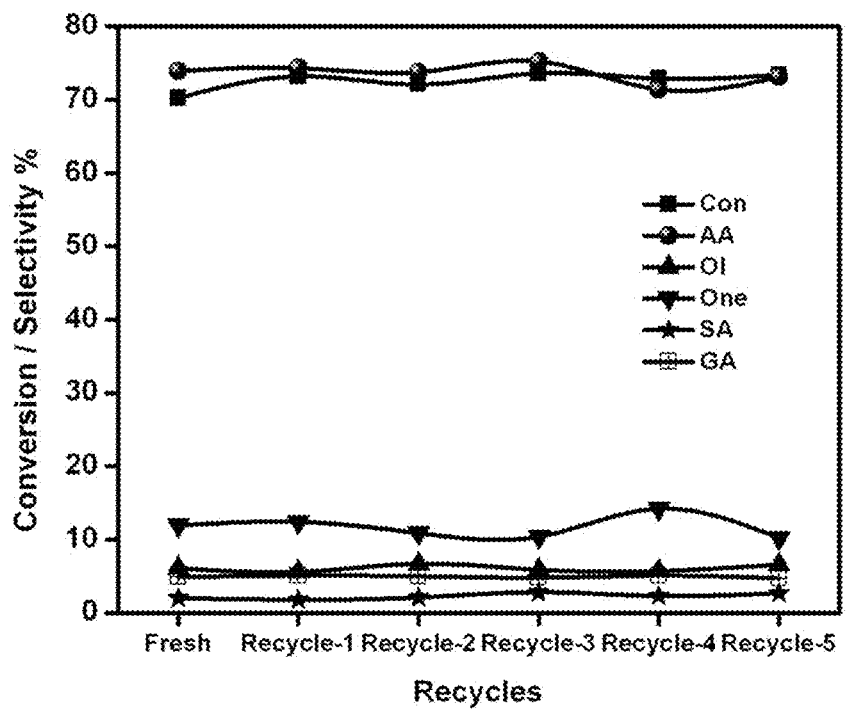
Fig: 18

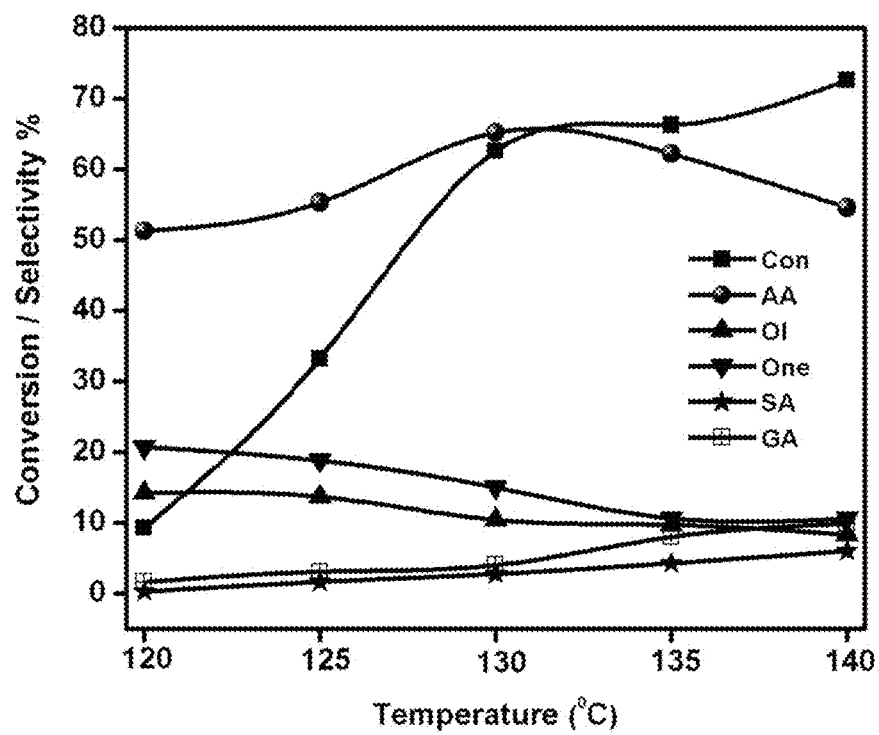
Fig: 19

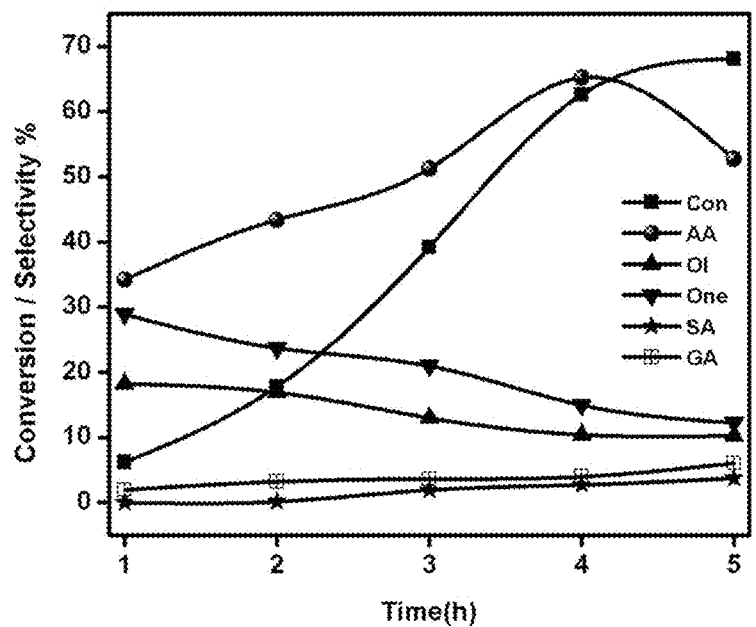
Fig: 20
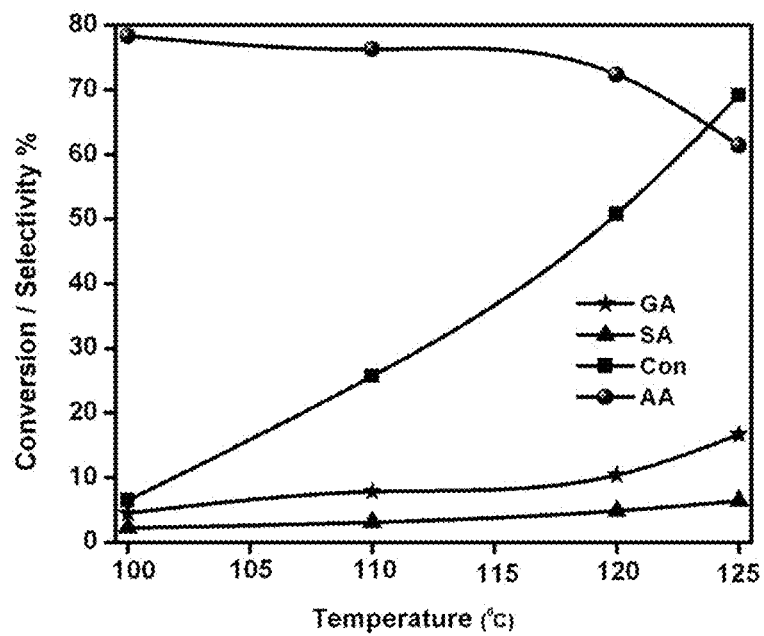
Fig: 21

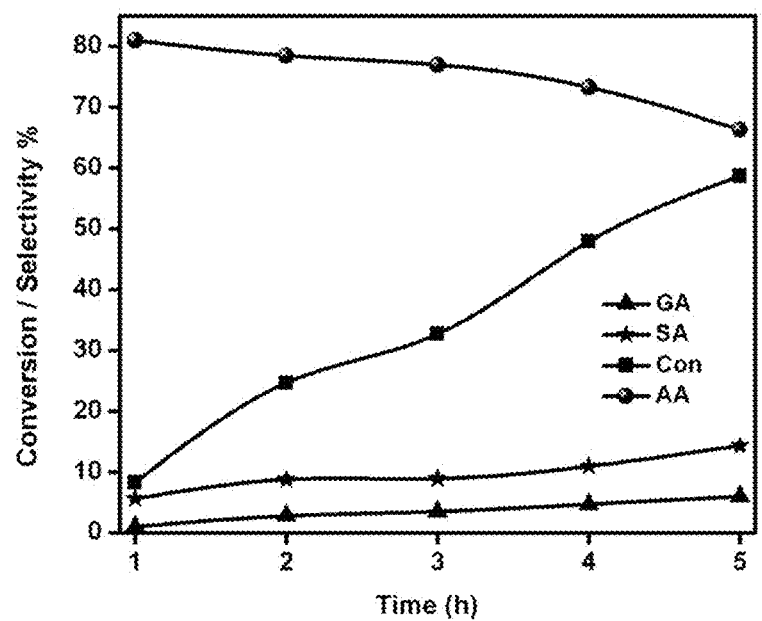
Fig: 22
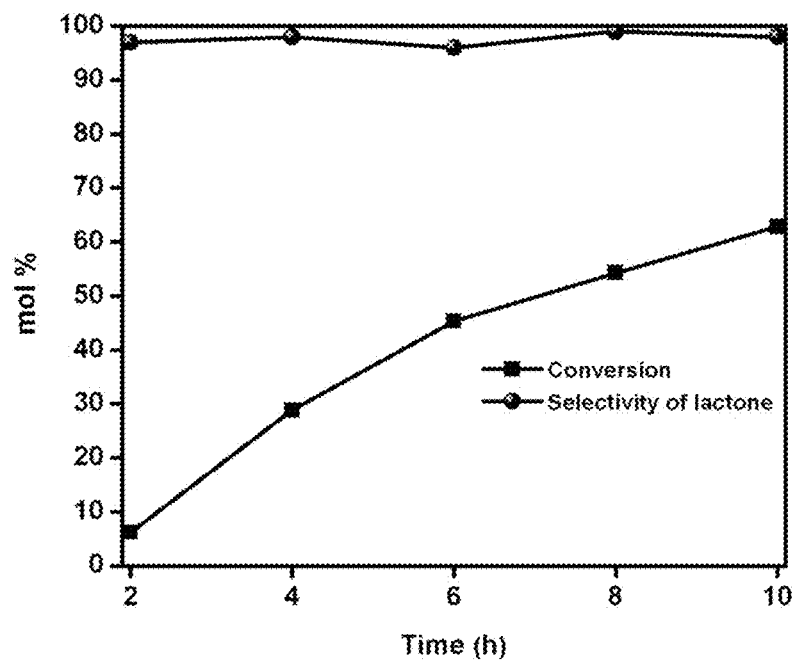
Fig: 23

US 9,944,617 B2

SELECTIVE AEROBIC OXIDATIONS USING CARBON NITRIDE NANOTUBES

PRIORITY CLAIM TO RELATED APPLICATIONS

This application is a U.S. national stage application filed under 35 U.S.C. § 371 from International Application Serial No. PCT/IN2014/000747, which was filed 2 Dec. 2014, and published as WO2015/083185 on 11 Jun. 2015, and which claims priority to Indian Application No. 3490/DEL/2013, filed 2 Dec. 2013, which applications and publication are incorporated by reference as if reproduced herein and made a part hereof in their entirety, and the benefit of priority of each of which is claimed herein.

FIELD OF THE INVENTION

The present invention relates to an improved oxidation process using carbon nitride nanotubes as metal free catalyst and molecular $O_2$ as the oxidant to obtain desired adipic acid and other oxygenated hydrocarbons with improved conversion and selectivity.

BACKGROUND AND PRIOR ART

Selective oxidation of hydrocarbons is an important process in the chemical industry, as it helps in the production of many useful chemicals like alcohols, aldehydes and carboxylic acids. Though there were innumerable numbers of publications/patents that deal with this area, it still remains a very important research challenge as many processes need green chemical routes and cost effective manufacturing. As a result, there is a drive to develop green and efficient processes for the oxyfunctionalization of hydrocarbons. Usually; efficient activation of an alkane requires precious metal catalysts and strong oxidizing agents ($HNO_3$, TBHP, and $H_2O_2$). Currently, partial oxidation processes are conducted either in gas phase or liquid phase using homogeneous/heterogeneous catalysts. Since molecular oxygen is cheap and abundant, it is the most practicable oxidant for partial oxidation processes. But, most of the heterogeneous catalyst based processes offer poor selectivity to the desired product when molecular oxygen is used as oxidant. Large quantities of energy are needed to separate the desired product from unwanted side products, leading to not only waste generation but also inefficient use of starting materials. Hence, achieving desired product selectivity remains an important task.

Adipic acid (AA) is an important selective oxidation product that is obtained from cyclohexane. Major part of AA produced is used as a precursor for the synthesis of Nylon-6,6. In addition, AA is widely used for the production of polyesters, polyurethane resins, plasticizers in the production of polyvinyl chloride (PVC) and polyvinyl butyral (PVB). Present day processes for AA involve multiple steps and also use highly corrosive acids. Thus, developing novel, clean and green routes for AA production is an important research theme.

The current industrial process for AA production is based on the catalytic oxidation of a mixture of cyclohexanol and cyclohexanone which is referred as KA oil (Ketone/alcohol). The KA oil in turn is obtained on partial oxidation of cyclohexane. Further oxidation of the KA oil to adipic acid is performed using 50-65% $HNO_3$ as oxidant in the presence of Cu (II) and ammonium metavanadate as catalysts. The selectivity to adipic acid based on KA oil is very high yielding only small quantities of glutaric acid as by-product. But, main drawback of nitric acid oxidation process is the stoichiometric reduction of $HNO_3$ to $NO_x$ in the form of greenhouse gas nitrous oxide ($N_2O$). The amount of $N_2O$ produced is around 300 kg per tonne of adipic acid, which also depends on the amount of catalyst and composition of the KA oil used.

In addition to the commercial process, there are alternative routes for producing AA. For example, AA can be obtained by direct oxidation of cyclohexene using hydrogen peroxide using a phase transfer catalyst. It can also be prepared by dimerization of methyl acrylate, carbonylation of butadiene and by bio catalytic fermentation of glucose. The oxidation of KA oil also can be carried out with oxygen as the oxidant, in place of nitric acid, using catalytic amounts of Co and Mn acetate, at 70-80° C. in acetic acid as solvent. However, acetic acid as solvent poses severe corrosion problems, particularly when combined with the Mn and Co salts. Moreover, most of these approaches results in poor selectivity (30-50%) towards the desired product. In addition, use of soluble homogeneous catalysts leads to its leaching during the course of the reaction, hampering recycling of the catalysts.

Nitrogen doped carbons were reported to have diverse applications in catalysis, particularly as electro catalysts, photo catalysts and as heterogeneous catalysts. Nitrogen containing carbons have received greater attention for oxyfuctionalization of hydrocarbons, as they are able to activate oxygen molecules without the assistance of any metals.

Article titled "Metal-free activation of dioxygen by graphene/g-$C_3N_4$ nanocomposites: functional dyads for selective oxidation of saturated hydrocarbons" by X H Li et al. published in *J. Am. Chem. Soc.*, 2011, 133 (21), pp 8074-8077 reports graphene sheet/polymeric carbon nitride nanocomposite (GSCN) functions as a metal-free catalyst to activate $O_2$ for the selective oxidation of secondary C—H bonds of cyclohexane. By fine-tuning the weight ratio of graphene and carbon nitride components, GSCN offers good conversion and high selectivity to corresponding ketones. Besides its high stability, this catalyst also exhibits high chemoselectivity for secondary C—H bonds of various saturated alkanes and, therefore, should be useful in overcoming challenges confronted by metal-mediated catalysis.

Article titled "Boron- and fluorine-containing mesoporous carbon nitride polymers: metal-free catalysts for cyclohexane oxidation" by Y Wang et al. published in *Angewandte Chemie International Edition*, Volume 49, Issue 19, pages 3356-3359, Apr. 26, 2010 reports N-doped carbon materials can catalyze the oxidation of cyclohexane (CyH) with $H_2O_2$ as an oxidizing agent to produce the KA oil with >99% selectivity. The boron- and fluorine-enriched carbon nitride polymeric semiconductor synthesized by a facile one-step process using 1-butyl-3-methylimidazolium tetrafluoroborate as a soft template. The resulting materials show an advantageous "morel-like" mesopore structure (see picture) with narrow pore size distribution and good photoactivity under visible light. These materials are also good catalysts for the selective oxidation of cyclohexane.

Article titled "Nitrogen-, phosphorous- and boron-doped carbon nanotubes as catalysts for the aerobic oxidation of cyclohexane" by Y Cao et al. published in *Carbon*, Volume 57, June 2013, Pages 433-442 reports nitrogen-, phosphorous- and boron-doped carbon nanotubes (N-CNTs, P-CNTs and B-CNTs) prepared by a chemical vapor deposition method using xylene as carbon source and aniline-NH3, triphenyl phosphine and triethyl borate as nitrogen, phosphorous and boron precursors, respectively. N- and P-CNTs are active for the oxidation of cyclohexane in the liquid phase with molecular oxygen as oxidant. The highest mass-normalized activity, 761 mmolg-1 h-1, achieved over N-CNTs synthesized from aniline in an $NH_3$ atmosphere, while the highest surface-area-normalized activity, 28 mmolm-2 h-1, was observed over P-CNTs. B-doping does not improve the activity of CNTs. The effect of the number of nitrogen functionalities and defects was investigated to reveal the structure—activity relationship of the doped CNTs.

Article titled "Graphite as a highly efficient and stable catalyst for the production of lactones" by Y F Li et al. published in Carbon, Volume 55, April 2013, Pages 269-275 reports that the carbon materials carbon nanotubes (CNTs), graphite, and activated carbon tested as metal-free catalysts. They showed excellent activity and selectivity in the Baeyer-Villiger (B-V) oxidation of cyclohexanone at room temperature using dioxygen ($O_2$) as oxidant and benzaldehyde as sacrificial agent. Among them graphite found to be the most suitable for the formation of lactones from cyclic ketones, showing good recyclability and reusability. The use of the metal-free catalysts enables a green process for the production of lactones from ketones under mild reactions.

Article titled "Solvent-free and metal-free oxidation of toluene using $O_2$ and g-$C_3N_4$ with Nanopores: Nanostructure Boosts the Catalytic Selectivity" by X H Li published in ACS Catal., 2012, 2 (10), pp 2082-2086 reports solvent-free oxidation of the primary C—H bonds in toluene to benzaldehyde has been achieved by using the metal-free catalyst g-$C_3N_4$ and $O_2$. It is the nanostructure of g-$C_3N_4$ that boosts the high selectivity by tuning the homogeneous oxidation to hetergeneous oxidation and capturing all free .$O_2$— radicals to effectively suppress the over oxidation of aldehydes.

Article titled "Selective catalysis of the aerobic oxidation of cyclohexane in the liquid phase by carbon nanotubes" by H Yu et al. published in *Angewandte Chemie International Edition*, Volume 50, Issue 17, pages 3978-3982, Apr. 18, 2011 reports Carbon nanotubes (CNTs) catalyze the aerobic oxidation of cyclohexane into cyclohexanol, cyclohexanone, and adipic acid with excellent activity and controllable selectivity. Nitrogen doped multi walled carbon nano tubes as catalysts gave higher yields of AA compared to gold catalysts. For instance, at 125° C. and 15 bar of $O_2$ pressure, 45% cyclohexane conversion with 60% AA selectivity was observed.

However, high cost of the catalysts and requirement of solvent are the main drawbacks of these above catalysts. Therefore, there is need to develop a green process and a catalyst for the selective oxidation with improved yields.

OBJECTIVE OF INVENTION

The main objective of the present invention is to provide an improved oxidation process using carbon nitride nanotubes as metal free catalyst and molecular $O_2$ as the oxidant to obtain desired adipic acid and other oxygenated hydrocarbons in higher yield.

SUMMARY OF THE INVENTION

Accordingly, the present invention provides a single step and metal free oxidation process for the preparation of oxygenated hydrocarbons with improved conversion and selectivity which comprises; reacting the substrate with molecular $O_2$ in presence of carbon nitride nanotubes catalyst and a solvent.

In an embodiment of the present invention the process is carried out at temperature 100-140° C.

In one embodiment of the present invention 25-100 mg carbon nitride nanotubes catalyst was used for 0.15 mole of substrate.

In another embodiment of the present invention the solvent is selected form acetonitrile and acetone.

Still in another embodiment of the present invention oxygenated hydrocarbons is selected from the group consisting of acids, ketones and lactones.

Still in another embodiment of the present invention the acid is adipic acid when substrate used is cyclohexane or cyclohexanone.

Still in another embodiment of the present invention ketones is 2-hexanone when substrate used is n-hexane.

Still in another embodiment of the present invention lactones is caprolactone when substrate used is cyclohexanone in the presence of benzaldehyde.

Still in another embodiment of the present invention selectivity of acids, ketones and lactones is in the range of −10-90%.

Still in another embodiment of the present invention conversion of n-hexane, cyclohexanone and cyclohexane is in the range of −10-70%.

BRIEF DESCRIPTION OF THE DRAWINGS

FIG. 1 depicts XRD pattern carbon nitride nano tubes.

FIG. 2 depicts XRD spectra of (a) melamine, (b) nano fiber and (c) nano tube.

FIG. 3 depicts Infrared spectra of (a) melamine, (b) nano fiber and (c) nano tube.

FIG. 4 depicts SEM images of carbon nitride nanotubes.

FIG. 5 depicts TEM images of carbon nitride (a & b) and carbon nano fiber (c).

FIG. 6 depicts XPS of nitrogen 1 s carbon nitride.

FIG. 7 depicts UV-Vis spectra of carbon nanotube.

FIG. 8 depicts PI spectra of carbon nanotube.

FIG. 9 depicts TGA plot of melamine nano fibers.

FIG. 10 depicts Temperature programmed desorption of $CO_2$.

FIG. 11 depicts Cyclic voltametric study (in KOH) of the carbon nitride (a); linear sweep cyclic voltammetry.

FIG. 12 depicts CV of catalyst in 0.5M $HClO_4$ solution (a); Linear sweep cyclic voltammetry.

FIG. 13 depicts Effect of temperature on adipic acid yield during CH oxidation. Conditions: Acetonitrile solvent 6.1 g, catalyst=50 mg, 4 h, 20 bar $O_2$, cyclohexane 12.6 g FIG. 14 depicts Effect of reaction time on adipic acid yield. Conditions: Cyclohexane=12.6 g, Acetonitrile=6.1 g, 130° C., Catalyst=50 mg, 20 bar $O_2$.

FIG. 15 depicts Effect of catalyst content on adipic acid yield. Conditions: Cyclohexane=12.6 g, Acetonitrile=6.1 g, 130° C., 4 h, 20 bar $O_2$.

FIG. 16 depicts Effect of substrate to solvent mole ratio on AA yield. Conditions: Cyclohexane, Acetonitrile, catalyst=50 mg, 130° C., 4 h, 20 bar $O_2$ FIG. 17 depicts Effect of $O_2$ pressure on AA yield. Conditions: Cyclohexane=12.6 g, Acetonitrile=6.1 g, Catalyst=50 mg, 130° C., 4 h, FIG. 18 depicts Recyclability study of the catalyst in CH oxidation. Conditions: Cyclohexane=12.6 g, Acetonitrile=6.1 g, catalyst=50 mg, 130° C., 4 h, 20 bar $O_2$.

FIG. 19 depicts Effect of reaction temperature on CH conversion and AA yield.

Conditions: Cyclohexane=15.58 g, 4 h, Catalyst=50 mg, 20 bar $O_2$

FIG. 20 depicts Effect of reaction time on CH conversion and AA yield. Conditions: Cyclohexane=15.58 g, 130° C., Catalyst=50 mg, 20 bar $O_2$ FIG. 21 depicts Effect of temperature on cyclohexanone oxidation.

Conditions: cyclohexanone 9 g, Acetonitrile 7 g, water=2 g, 4 h, CNNT catalyst 50 mg, 20 bar $O_2$.

FIG. 22 depicts Effect of time on selective cyclohexanone. Conditions: 9 g cyclohexanone, Acetonitrile 7 g, 120° C., CNNT 50 mg, 20 bar $O_2$.

FIG. 23 depicts Effect of time on the yield of Caprolactone. Conditions: 10 mmol cyclohexanone, 20 mmol benzaldehyde, 50 mg Catalyst, 50° C., 10bar $O_2$.

DETAILED DESCRIPTION OF THE INVENTION

The present invention provides an improved oxidation process for the preparation of acids, ketones and lactones with improved conversion and selectivity which comprises reacting the substrate with molecular $O_2$ in presence of catalytic amount carbon nitride nanotubes and a solvent.

The present invention provides improved oxidation process for the preparation of acids, ketones and lactones with improved conversion and selectivity wherein the acids, ketones and lactones are selected from adipic acid, caprolactone and 2-hexanone.

The present invention provides an improved process for the preparation of adipic acid from cyclohexane using carbon nitride nanotubes (CNNT) as metal free catalyst and molecular $O_2$ as the oxidant.

The improved process for the preparation of adipic acid from cyclohexane using carbon nitride nanotubes (CNNT) provide better selectivity 72.4% and conversion up to 69.7%.

The present invention provides an improved process for the preparation of adipic acid from cyclohexanone using carbon nitride nanotubes (CNNT) as metal free catalyst and molecular $O_2$ as the oxidant. The process is same as followed in cyclohexane but the temperature required to get maximum yield of adipic acid is less. The present invention provides an improved process for the preparation of 2-hexanone from n-hexane using carbon nitride nanotubes (CNNT) as metal free catalyst and molecular $O_2$ as the oxidant.

The improved process for the preparation of 2-hexanone from n-hexane using carbon nitride nanotubes (CNNT) shows 44.3% conversion of n-hexane and 24.9% selectivity at reaction time 8 hrs.

The present invention provides an improved process for the preparation of caprolactone from cyclohexanone using carbon nitride nanotubes (CNNT) as metal free catalyst and molecular $O_2$ as the oxidant.

The improved process for the preparation of caprolactone from cyclohexanone using carbon nitride nanotubes (CNNT) shows 98% selectivity and conversion 62.8% in conversion of cyclohexanone at reaction time 10 hrs.

The following examples are given by way of illustration of the working if the invention is actual practice and shall not be construed to limit the scope of the present invention in anyway.

EXAMPLES

Example 1

Preparation of Catalyst

Melamine (0.9068 g) was dissolved in ethylene glycol (40 ml) to obtain a saturated solution at 30° C. temperature. To this, aqueous nitric acid (120 ml of 0.12 M) was added drop wise to get white precipitate. This was washed by ethanol to remove residual nitric acid and ethylene glycol. Subsequently, the product was dried at 60° C. for 6 h and calcined at 350° C. for 3 h in air.

Characterization of Catalyst

XRD

The structural aspects of the catalysts were investigated by powder X-ray diffraction. FIG. 1 shows two peaks. The most intense peak at around 27.2° corresponds to interlayer distance d=0.336 nm, close to the characteristic peak of the (002) plane in the g-$C_3N_4$ structure (d=0.336 nm) which is reported for graphite-like carbon nitride (d=0.321, or 0.328 nm). The peak characteristic to in-plane structural packing motif of the nanotube appears at 17.8° (d=0.49 nm), close to the theoretical d=0.47 nm. So it is evident from XRD that the present nanotube acquires a s-triazine based structure rather than the reported commonly known tri-s-triazine unit.

IR

The IR spectra of melamine, nanofibers and nano tubes are illustrated in

FIG. 3. The strong absorption peaks in the 3330-3550 $cm^{-1}$ range are attributed to the stretching vibrations of $NH_2$ and NH groups. The above modes were absent in the nanotubes, suggesting that deamination occurs during calcination of nanofibers, which destroys most of the N—H bonds. FIG. 3 (a) represents melamine, (b) its nano fiber and (c) its nanotube.

SEM and TEM

The FE-SEM images in FIG. 4 reveals high yield production of elegant, flexible and ultra-long nanotubes. The nanotube is of a general average outer diameter of 1.5μ with lengths up to several millimeter. The magnified TEM image in FIG. 5 reveals that carbon nitride nanotube wall consists of several layers analogous to multiwall carbon nanotubes. The d-spacing's (0.36 nm & 0.49 nm) obtained from TEM images are in agreement with the XRD results.

XPS

Similarly N 1 s spectrum (FIG. 6) has three peaks at around 398.5, 399.95 and 401.0 ev which correspond to pyridinic, pyrrolic and graphitic respectively. The first two peaks may be attributed to $sp^3$ C—N bonds while the third one is due to a N-$sp^2$C bond, which proves that there is bonding between the nitrogen and carbon atoms.

UV-Visible and Photoluminescence Spectroscopy

FIGS. 7 and 8 illustrates the UV-vis spectra and photoluminescence of carbon nitride. It shows the absorption edge at 440 nm centered around 300 nm, originating from π-π* electronic transition in the aromatic 1,3,5-triazine compound.

$CO_2$-TPD

The basicity of the carbon nanofibre catalyst was determined by TPD of $CO_2$. FIG. 10 shows that significant concentration of basic sites is present on the catalyst. The basic sites are the free $NH_2$ on surface of the catalyst which were not polymerized.

Cyclic Voltammetry

The electro catalytic activity of the synthesized CNNT's was examined using cyclic voltammetry (CV) and rotating disc electrode (RDE) voltammetry in FIGS. 11 and 12. The onset potential of the material was found to be around 0.6V. The above described CV measurements show that the material has redox sites that can reduce $O_2$ even in the absence of any metal.

Catalyst testing: Selective oxidation reactions were performed in a 50 ml Parr autoclave. Reactant along with the catalyst was transferred to the haste alloy reactor. After heating the reaction mixture to the desired temperature, reactor was pressurized with oxygen. Conversion of reactant and product selectivity's was calculated based on the GC and HPLC analysis respectively. Products were analyzed using Agilent HPLC, equipped with RI detector and Rezex ROA-Organic Acid H$^+$ column (300 mm×7.8 mm) with 5 mM $H_2SO_4$ as the mobile phase at a flow rate of 0.6 mL·min$^{-1}$.

Example 2

Synthesis of Adipic Acid from Cyclohexane

Initially 12.6 of cyclohexane, 6.1 g of acetonitrile and 50 mg of catalyst was placed in 50 mL parr autoclave. The mixture was heated to desired temperature, reactor was pressurized with oxygen. After the completion of reaction products are identified by HPLC and GC:

Selective oxidation of cyclohexane (CH) to adipic acid was carried out using carbon nitride nano tube catalysts. Optimization of various experimental parameters was carried out to optimize the adipic acid yields.

Effect of Temperature: The effect of temperature on selective oxidation of cyclohexane is shown in FIG. 13. It is seen that CH conversion as well as AA selectivity increased initially with temperature, but AA yield drops after reaching a maximum. On the other hand, CH conversion increased continuously with temperature with about 24% at 125° C. to 86 mol % at 140° C. Cyclohexanol and cyclohexanone were also found in the product, particularly at low reaction temperatures, implying that the K-A (Ketone-Alcohol) oil formed as primary product, which is oxidized to AA in a subsequent step. When the temperature is raised, the rate of consecutive oxidation increased, accelerating the conversion of cyclohexanol to cyclohexanone and then to AA. Hence, the AA selectivity increased with increasing temperature up to 130° C. However, further rise in temperature to 140° C. led to the formation of undesired products, mainly the glutaric and succinic acids. These results guide us to an optimum temperature of 130° C., where we can get reasonably high conversion along with very good selectivity to AA. Hence, this temperature was chosen for further investigations.

Effect of Time: Effect of reaction time on conversion of cyclohexane and AA selectivity is shown in FIG. 14. The AA selectivity increased with time, reaching a maximum after 4 hours. The selectivity's of cyclohexanol (OI) and cyclohexanone (One) decreased with time. Between 2-4 h, the selectivity of AA increased at the expense of K-A oil. After 4$^{th}$ hour, the AA selectivity decreased due to AA degradation to glutaric acid (GA) and succinic acid (SA). This data shows that the KA concentration was high in the initial period (induction period) of the reaction, which subsequently converts in to AA with increasing TOS.

Effect of catalyst concentration: Influence of catalyst concentration in the reaction mixture is shown in FIG. 15. With increasing catalyst amount, conversion of cyclohexane has increased, but reached a maximum at around 50 mg for 12.6 g of substrate (CH). Though the AA selectivity was related to catalyst content at least upto 50 mg, the selectivity to degradation byproducts was almost independent to the catalyst content. With the increase in the catalyst content from 25-50 mg, the AA selectivity increased corresponding to a reduction in K-A oil. Increasing the catalyst content further to 75-100 mg led to a marginal drop in AA selectivity because of its transformation to by-products like GA and GA. Therefore, it is possible to conclude that the selectivity of byproducts depends more on contact time but not on catalyst content.

Effect of substrate to solvent ratio: As shown in FIG. 16, with increase in mole ratio of substrate to solvent, there was a negative influence on conversion. At 1:1 molar ratio, the selectivity of AA was found to be maximum. At lower or higher mole ratios, selectivity of AA was affected. So, there was a considerable effect of solvent on the above reaction.

Effect of oxygen pressure: FIG. 17 demonstrates the influence of oxygen pressure on the performance. It is evident that with increase in oxygen pressure from 5 to 20 bar, conversion of cyclohexane has increased significantly from 10 to 70 mol %. At lower oxygen partial pressure, K-A oil was found in higher concentration. However, higher pressure of $O_2$ led to the over-oxidation resulting in the formation of other dicarboxylic acids (GA and SA). At 20 bar, AA has formed as major a product. This clearly shows that oxygen pressure plays vital role in AA yield.

Recyclability of the Catalyst:

To check the reusability and stability of the catalysts, recycling tests were carried out, after washing the catalyst with acetonitrile prior to its re-use. The catalyst was used for five such cycles. There was no significant change either in catalyst activity or AA selectivity even after 5th recycle as can be seen from FIG. 18.

Solvent Free Oxidation of Cyclohexane

For a selective oxidant process to be called as 'green', in addition to use environmental friendly oxygen source such as $O_2$, no solvent should be used for carrying out the reaction. If no solvent is used, energy saving also occurs, as there is no need to separate the solvent from products or un-reacted substrates. Hence, we have conducted selective oxidation of cyclohexane in solvent free conditions. Effect of various parameters has been investigated; results of these experiments are illustrated below.

Effect of Temperature:

Effect of temperature on the yield of AA in solvent free condition is show in FIG. 19. It can be clearly seen, as was the case with solvent based reaction, CH conversion increased with temperature upto 71 mol % at 140° C. The AA selectivity also increased, but it reached to a maximum at 130° C., there after it decreased with temperature. Cyclohexanol and one were present in significant quantities at low reaction temperature, as they are the primary products of the reaction. Since, at higher temperatures, sequential oxidation is favoured, it leads to the formation of AA from cyclohexanol and cyclohexanone. As a result, the AA selectivity increased with increasing temperature up to 130° C. Further increase in temperature to 135-140° C. leads to the formation of undesired GA and SA products. These results shows that even in the absence of solvent, reaction temperature of 130° C. seems to be optimum for achieving high CH conversion and AA selectivity. However, both these values are on lower side as compared to the conversion and yields achieved with solvent.

Effect of Time:

The effect of reaction time on CH conversion and AA yield in solvent free conditions is depicted in FIG. 20. With TOS, conversion of cyclohexane has increased monotonously, but the AA selectivity increased to a maximum after 4$^{th}$ hour and dropped further on stream. The selectivity's of One and OI were also decreased with increasing time on stream. Between 1-4 h, the AA selectivity increased at the expense of KA oil. This result indicates that the AA formation is favoured with increasing reaction time. But, after 4$^{th}$ hour, the AA selectivity decreased due to its degradation to by products such as GA and SA.

Example 3

Comparison of Various Catalysts in the Selective Oxidation of Cyclohexane

TABLE 1

Performance of various catalysts in selective oxidation of cyclohexane

| Sr. No | Catalyst | Cyclohexane: Acetonitrile | Conv. mol % | Selectivity (mole %) | | | | |
|---|---|---|---|---|---|---|---|---|
| | | | | ol | one | Glutaric acid | Succinic acid | Adipic acid |
| 1 | g-$C_3N_4$ | 1:1 (12.6:6.1 g) | 19.36 | 23.3 | 26.5 | 8.36 | 5.21 | 30.23 |
| 2 | Melamine carbon nano fibers(after $HNO_3$ treatment) | 1:1 (12.6:6.1 g) | 10.2 | 7.32 | 21.0 | 8.78 | 3.22 | 61.24 |
| 3 | Carbon nitride nano tubes[$] | 1:1 (12.6:8.7 g) | 89.5 | 10.2 | 18.23 | 13.45 | 5.96 | 45.3 |
| 4 | Mesoporous Carbon nitride[#] | 1:1 (12.6:6.1 g) | 24.2 | 8.3 | 22.5 | 4.0 | 2.1 | 58.4 |
| 5 | Carbon nitride nano tubes* | 1:1 (12.6:6.1 g) | 0.6 | — | — | — | — | — |
| 6 | Carbon nitride nano tubes[@] | 1:1 (12.6:6.1 g) | 69.7 | 4.78 | 9.95 | 6.06 | 3.54 | 72.4 |

Conditions: 130° C., 4 h, 20 bar $O_2$, 50 mg catalyst
[$]Acetone as solvent,
[@]Acetonitrile as solvent
[#]using P123 polymer and H2SO4
*butylated hydroxytoluene (10 mol %)

Under blank reaction conditions, the conversion of cyclohexane was bare minimum. With g-$C_3N_4$ as catalyst, CH conversion and AA selectivity's were low. The reaction rate increased with acetone as solvent, but AA selectivity was low. Mesoporous carbon nitride was found to be inefficient for the above catalyst and the usage of radical scavenger BHT terminates the oxidation process by capturing the superoxide radical which shows the reaction is initiated by superoxide radical.

Example 3

Synthesis of Adipic Acid from Cyclohexanone

Initially 9 g of cyclohexanone, 7 g of acetonitrile, 2 g of water and 50 mg of catalyst was placed in 50 mL parr autoclave. The mixture was heated to desired temperature, reactor was pressurized with oxygen. After the completion of reaction products are identified by HPLC:

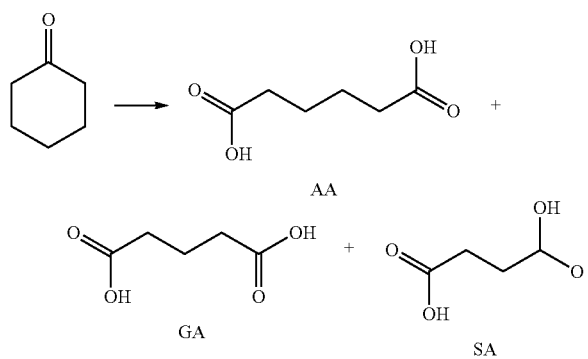

Effect of temperature: Effect of the reaction temperature on catalytic activity in the selective oxidation of cyclohexanone to AA is shown in FIG. 21. Increasing the reaction temperature promotes conversion of cyclohexanone. Selectivity of AA reaches maximum at 120° C., but decreases beyond this temperature. The decrease in AA selectivity is attributed to the decarboxylation at higher temperatures to form $C_2$, $C_4$ dicarboxylic acids.

Effect of reaction time on catalytic activity: Effect of reaction time on catalytic activity of CNT in the selective oxidation of cyclohexanone is given in FIG. 22. Conversion of cyclohexanone has increased with increasing time on stream, while AA yield was found to decrease with time as a result of increased decarboxylation of AA. So in order to achieve higher amount of AA, choosing a particular reaction time is important in this reaction.

Example 4

Synthesis of Caprolactone from Cyclohexanone

The CNNT catalyst was also tested for Bayer-Villiger oxidation of cyclohexanone to Caprolactone. About 10 mmol of cyclohexanone, 20 mmol of benzaldehyde and 50 mg of catalyst was placed in 50 mL parr autoclave. The mixture was heated to desired temperature, reactor was pressurized with oxygen. After the completion of reaction, products are identified by GC

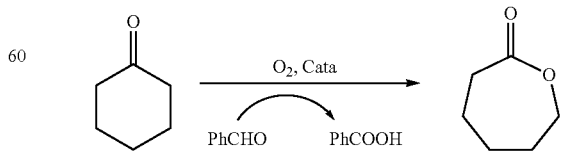

Effect of time on caprolactone yield: FIG. 23 shows the effect of reaction time on Bayer-Villiger oxidation of cyclohexanone to caprolactone cyclohexanone to E-caprolactone. With increase in time, the conversion of cyclohexanone has increased.

Example 5

Synthesis of 2-hexanone from n-hexane

Initially 2.5 g of n-hexane, 12.5 mL of acetonitrile and 100 mg of catalyst was placed in 50 mL parr autoclave. The mixture was heated to desired temperature, reactor was pressurized with oxygen. After the completion of reaction, products are identified by HPLC and GC:

The oxidation of n-hexane with the carbon nitride nanotube catalyst was conducted with $H_2O_2$ and $O_2$ as oxidants, the results of which are shown in Table 3.

TABLE 3

Selective oxidation of n-hexane using CNNT catalysts

| Sr. No | Oxidant | Time (h) | Conversion | Selectivity % 2-hexanone |
|---|---|---|---|---|
| 1 | $H_2O_2$ (3 moles) | 4 | 37.8 | 24.3 |
|   |   | 8 | 57.7 | 26.9 |
| 2 | $H_2O_2$ (2 moles) | 4 | 16.3 | 31.6 |
|   |   | 8 | 30.8 | 30.4 |
| 3 | $H_2O_2$ (1 mole) | 4 | 6.9 | 32.5 |
|   |   | 8 | 15.1 | 33.7 |
| 4 | $O_2$ (15 bar) | 4 | 26.9 | 22.6 |
|   |   | 8 | 44.3 | 24.9 |

Conditions: 2.5 g n-hexane, 12.5 ml acetonitrile, 100 mg CNNT, 100° C.

In the case of $H_2O_2$ oxidations, conversion of n-hexane has increased with increasing $H_2O_2$/substrate ratio. Conversion of n-hexane also increased with increasing reaction time. When oxidation was performed with molecular oxygen, reasonable conversion of n-hexane was achieved with 2-hexanone as the product.

Advantages of Invention a. The present process facilitates selective oxidation of hydrocarbons and alcohols, particularly to get adipic acid from cyclohexane in a single step.
b. Metal free catalysts, hence there won't be any metal leaching problems.
c. Process uses non-corrosive solvents like acetonitrile.
d. Process also can be conducted without any solvent. Green and economic process.
e. Recyclable heterogeneous catalyst.

We claim:

1. A single step and metal free oxidation process for the preparation of an oxygenated hydrocarbon which comprises reacting a hydrocarbon substrate with molecular $O_2$ in presence of $C_3N_4$ (carbon nitride), nanotubes catalyst and a solvent.

2. The oxidation process as claimed in claim 1, wherein the process is carried out at temperature 100-140° C.

3. The oxidation process as claimed in claim 1, wherein 25-100 mg carbon nitride nanotubes catalyst was used for 0.15 mole of substrate.

4. The oxidation process as claimed in claim 1, wherein the solvent s selected form acetonitrile and acetone.

5. The oxidation process as claimed in claim 1, wherein the oxygenated hydrocarbon is selected from the group consisting of acids, ketones, aldehydes, and lactones.

6. The oxidation process as claimed in claim 1, wherein the oxygenated hydrocarbon is adipic acid and the hydrocarbon substrate is cyclohexane, cyclohexanone, cyclohexanol, or a combination of cyclohexanone and cyclohexanol.

7. The oxidation process as claimed in claim 1, wherein the oxygenated hydrocarbon is 2-hexanone and the hydrocarbon substrate is n-hexane.

8. The oxidation process as claimed in claim 1, wherein the oxygenated hydrocarbon is caprolactone and the hydrocarbon substrate is cyclohexanone in the presence of benzaldehyde.

9. The oxidation process as claimed in claim 5, wherein selectivity of acids, ketones and lactones is in the range of 10-90%.

10. The oxidation process as claimed in claim 1, wherein the hydrocarbon substrate is n-hexane, cyclohexanone, cyclohexanol, and cyclohexane and conversion of the substrate is in the range of 10-70%.

* * * * *